US00PP28306P2

(12) United States Plant Patent
Gray et al.

(10) Patent No.: US PP28,306 P2
(45) Date of Patent: Aug. 22, 2017

(54) FLORIBUNDA ROSE PLANT NAMED 'GRAYLLW'

(50) Latin Name: ***Rosa* hybrid**
Varietal Denomination: GRAyllw

(71) Applicants: John Charles Gray, Highfields (AU); Sylvia Elizabeth Gray, Highfields (AU)

(72) Inventors: John Charles Gray, Highfields (AU); Sylvia Elizabeth Gray, Highfields (AU)

( * ) Notice: Subject to any disclaimer, the term of this patent is extended or adjusted under 35 U.S.C. 154(b) by 0 days.

(21) Appl. No.: 14/999,235

(22) Filed: Apr. 14, 2016

(51) Int. Cl.
*A01H 5/02* (2006.01)

(52) U.S. Cl.
USPC ..... Plt./144

(58) Field of Classification Search
USPC ..... Plt./144
CPC ..... A01H 5/0222
See application file for complete search history.

*Primary Examiner* — Kent L Bell

(57) ABSTRACT

'GRAyllw' is a new and distinct floribunda type *Rosa* hybrid cultivar which is characterized by the combination of an upright to semi-weeping growth habit, excellent resistance to *Diplocarpon rosae*, nearly continuous flowering, white flowers with a yellow center, tightly cupped, double-type flowers, a light rose fragrance, and the stability of these characteristics from generation to generation. The new cultivar is generally suited to landscape applications.

2 Drawing Sheets

Latin name of genus and species: The Latin name of the genus and species of the novel variety disclosed herein is *Rosa* hybrid.

Variety denomination: The inventive variety of *Rosa* hybrid disclosed herein has been given the variety denomination 'GRAyllw'.

BACKGROUND OF THE INVENTION

The present invention relates to a new and distinct *Rosa* hybrid, floribunda rose cultivar, which has been given the variety denomination of 'GRAyllw'.

Parentage: 'GRAyllw' is a seedling selection which resulted from the controlled cross-pollination of an unnamed *Rosa* hybrid female breeding line and an unnamed *Rosa* hybrid male breeding line. Both parents, developed by the same inventor and never commercially released, exhibited traits deemed commercially significant and desirable.

After many years of trialing, the female parent was confirmed to possess a combination of desirable traits such as complete resistance to rose black spot disease, complete resistance to powdery mildew, and flowers with a strong citrus-like perfume borne on a bushy plant growing to 1.2 m tall and wide. The male parent was selected for use in breeding after trialing confirmed the presence of strong true-rose perfume and a bright, modern flower color. During the summer of 2010, the female parent was emasculated and was manually pollinated with pollen from the male parent. In autumn of 2010, seed was collected from hips produced by the female parent and a number of seedlings were grown to a mature size, including the claimed plant. These progeny were further evaluated for desirable traits such as black spot disease resistance and strong perfume, and in June of 2011 the claimed plant was first observed. In January of 2013, after further evaluation for desirable traits, the claimed plant was deemed to be garden-worthy and suited to widespread cultivation. It was given the denomination, 'GRAyllw'.

Asexual Reproduction: Asexual propagation of 'GRAyllw', by way of softwood stem cuttings, was first performed in May of 2011 at the inventor's nursery in Highfields, Australia. Through more than twelve subsequent generations, the unique features of this cultivar have proven to be stable and true to type.

SUMMARY OF THE INVENTION

The following characteristics have been repeatedly observed and represent the distinguishing characteristics of the new *Rosa* cultivar 'GRAyllw'. These traits, in combination, distinguish 'GRAyllw' as a new and distinct cultivar.

1. *Rosa* hybrid 'GRAyllw' exhibits an upright to semi-weeping growth habit; and
2. *Rosa* hybrid 'GRAyllw' exhibits excellent resistance to the plant pathogen, *Diplocarpon rosae*, commonly referred to as rose black spot disease; and
3. *Rosa* hybrid 'GRAyllw' exhibits nearly continuous flowering; and
4. *Rosa* hybrid 'GRAyllw' exhibits a tightly cupped, double-type flower; and
5. *Rosa* hybrid 'GRAyllw' exhibits white flowers with a yellow center; and
6. *Rosa* hybrid 'GRAyllw' exhibits flowers with a light rose fragrance.

DETAILED BOTANICAL DESCRIPTION

Figure 1:
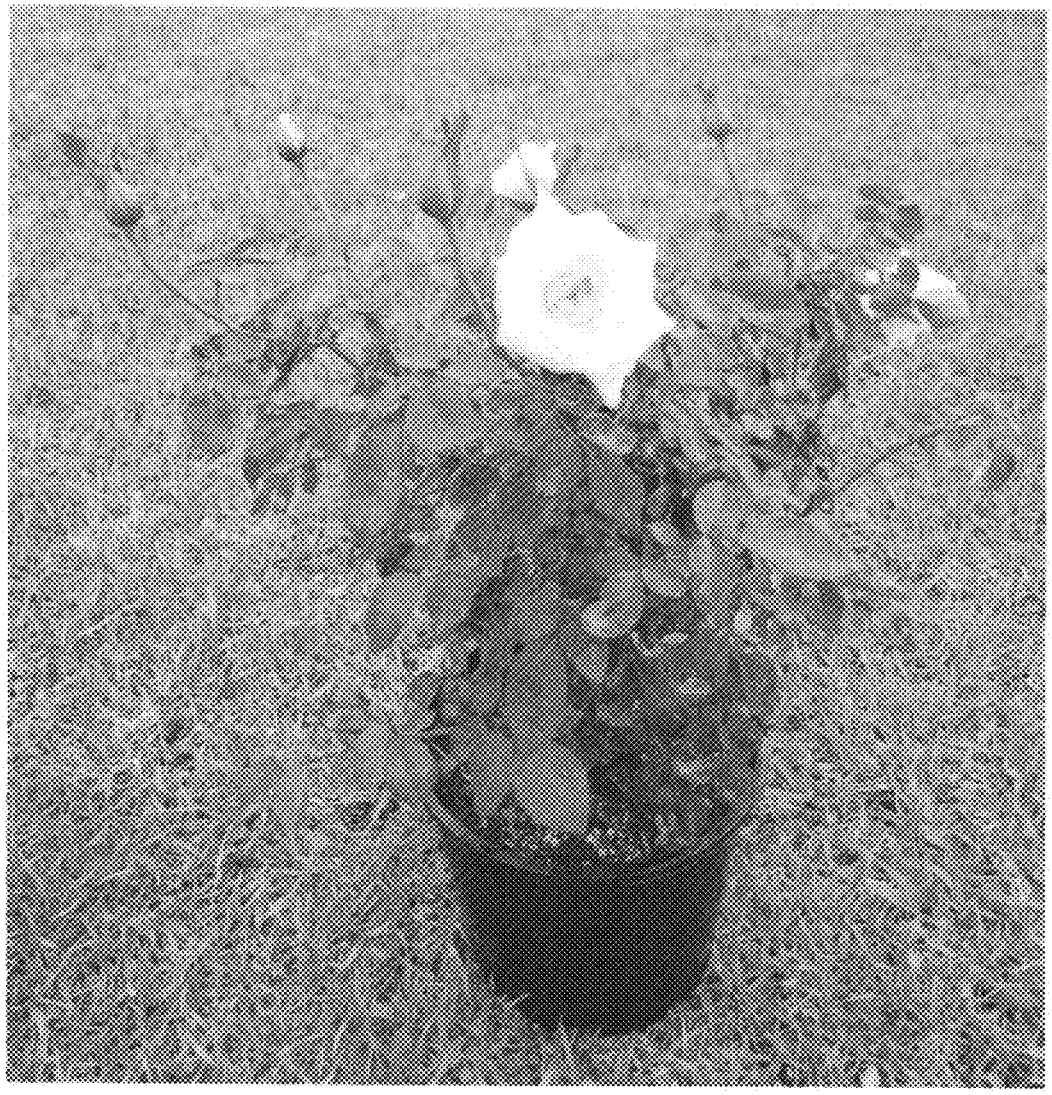
FIG. 1 illustrates, as nearly true as it is reasonably possible to make the same in color photographs of this type, an exemplary 5 month old 'GRAyllw' container-grown plant in a 20 cm pot, grown outdoors at the inventor's commercial nursery in Highfields, Australia.
Figure 2:
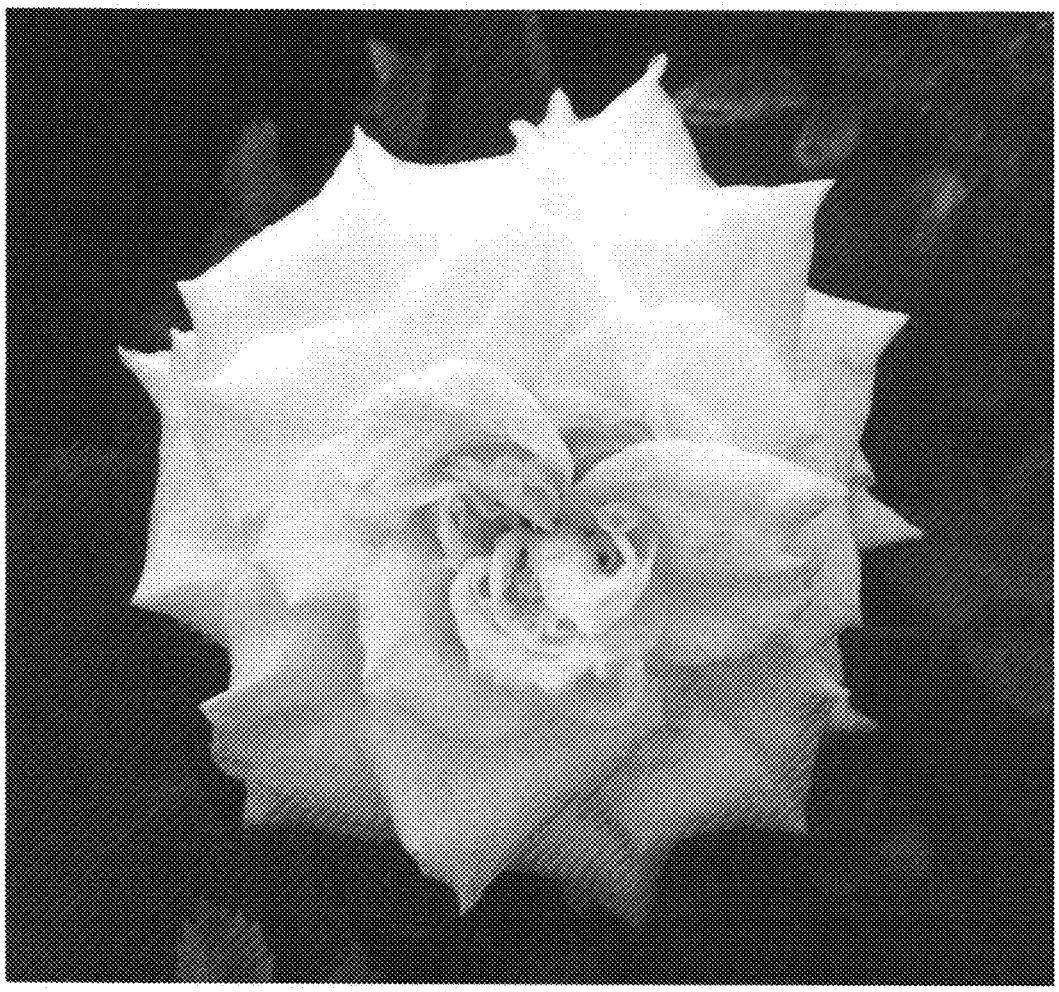
FIG. 2 illustrates, as nearly true as it is reasonably possible to make the same in color photographs of this type, the typical flower of 'GRAyllw'.

The following observations and measurements, made in February of 2016, describe averages of two own-root specimens of one year old 'GRAyllw' plants. The plants were grown outdoors in 20 cm containers, in a soilless pine bark based growing media, at the inventor's nursery in Highfields, Australia. No shade or supplemental light was provided. Temperatures ranged from approximately 17 to 35 degrees Celsius during the day and 7 to 18 degrees Celsius at night. Standard practices for irrigation, fertilizer and pest control were applied at appropriate times during the growing season. The plants were pruned three times during the growing season using accepted techniques for rose pruning.

Those skilled in the art will appreciate that certain characteristics will vary with older or, conversely, with younger plants. 'GRAyllw' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2007 Fifth Edition except where common terms of color are used.

A botanical description of 'GRAyllw' and comparisons with the parents and the most similar commercial cultivar of *Rosa* hybrid are provided below.

General plant description:

*Growth habit*.—Upright to semi-weeping.

*Growth rate*.—Approximately 1 year to reach 30 cm.

*Dimensions*.—33 cm tall and 55 cm wide.

*Environmental tolerance*.—Very good heat tolerance; cold hardiness is unknown.

*Disease resistance*.—Excellent resistance to powdery mildew (*Sphaerotheca pannosa*) and blackspot (*Diplocarpon rosae*).

*Propagation*.—Technique — Softwood stem cuttings. Time to initiate roots — About 13 days at approximately 21 degrees Celsius at root zone and 18 degrees Celsius ambient temperature. Time to produce a rooted cutting — About 25 days at approximately 21 degrees Celsius at root zone and 18 degrees Celsius ambient temperature.

Root system: White fibrous roots with many root hairs extending from lesser roots in a featherlike arrangement.

Branches:

*Branching habit*.—Irregular branching from mature branches, breaking first from the uppermost buds near the apex of each shoot.

*Quantity*.—Numerous.

*General dimensions*.—Approximately 30 cm long; 0.8 cm in diameter near the base and tapering to 0.5 cm.

*Immature branches*.—Diameter — Approximately 0.3 cm. Texture and pubescence — Smooth with prickles; moderately to heavily pubescent. Color — Near RHS N138D. Prickles — Density — Sparse to moderate. Color — Near RHS 177A. Shape — Concave. Texture — Smooth.

*Mature branches*.—Diameter — Approximately 0.8 cm, after one year. Texture and pubescence — Smooth and glabrous, with prickles. Color — Near RHS N138C. Prickles — Density — Moderate. Color — Near RHS 177A. Shape — Concave. Texture — Smooth.

Leaves:

*Arrangement*.—Alternate imparipinnate compound leaves.

*Quantity*.—Approximately 7 per mature branch.

*Attachment*.—Petiolate.

*Leaf internode length*.—2.5 cm.

*Dimensions*.—Approximately 7.0 cm long and 3.5 cm wide.

*Petiole*.—Dimensions — Average of 0.7 cm long and 0.1 to 0.2 cm wide. Color — Near RHS 139B. Texture and pubescence — Smooth and glabrous. Prickles — present. Stipitate glands — Not present.

*Stipule*.—Dimensions — 0.7 cm long and 0.2 cm wide. Color — Near RHS 144C. Texture and pubescence — Smooth and glabrous. Margins — Ciliate. Apex — Acuminate. Base — Winged. Prickles — Not present. Stipitate glands — Not present.

*Rachis*.—Dimensions — 0.5 cm long and 0.1 cm wide. Color — Near RHS 144D. Prickles — Not present. Stipitate glands — Not present.

*Leaflets*.—Quantity — Five leaflets on axillary leaves. Dimensions — Average size of the terminal leaflet is 2.6 cm long and 2.0 cm wide. Shape — Ovate. Apex — Acuminate. Base — Ovate. Margins — Serrated. Texture, pubescence and luster, adaxial surface — Smooth, glabrous, and semi-glossy. Texture, pubescence and luster, abaxial surface — Rough, glabrous, and matte. Juvenile foliage color, adaxial surface — Near RHS 135C. Juvenile foliage color, abaxial surface — Near RHS 138B. Mature foliage color, adaxial surface — Near RHS 136A. Mature foliage color, abaxial surface — Near RHS 138B. Venation — Pinnate. Venation color, adaxial surface — Near RHS 136A. Venation color, abaxial surface — Near RHS 138B. Petiolule — Dimensions — 0.1 cm long and 0.1 cm wide. Color — Near RHS 137A. Prickles — Not present. Texture — Smooth.

Inflorescence:

*Inflorescence type*.—Flowers are solitary.

*Blooming habit*.—Almost continuous from October through June in the southern hemisphere.

*Time to flower*.—6 to 8 weeks for a new stem to mature and flowering begins to occur once a stem matures.

*Peduncle*.—Dimensions — 5.0 cm long and 0.2 cm in diameter. Color — Near RHS 144B. Strength — Strong. Texture and pubescence — Smooth and glabrous. Prickles — None present.

Bud:

*Shape*.—Ovate.

*Size*.—2.5 cm long and 1.0 cm in diameter.

*Color*.—Near RHS 145B.

Flower:

*Calyx*.—General — Comprised of five polysepalous sepals, with two to three strong foliaceous appendages present on all sepals. Diameter of calyx — 0.6 cm. Sepals — Color, interior surface — RHS 149D. Color, exterior surface — RHS 145B. Dimensions — 2.0 cm long and 0.6 cm wide. Apex — Acuminate. Base — Flat at union with receptacle. Quantity — Five. Pubescence — Densely puberulent. Margins — Two to three strong foliaceous appendages. Stipitate glands — None present.

*Corolla*.—General shape of corolla — Irregularly rounded. Rate of opening — 6 days from bud to anthesis. Dimensions — Approximately 6 cm in diameter and 3 cm deep. Fragrance — Light rose scent. Lastingness — On the plant for 5 days after anthesis. Persistence — Self-cleaning. Petals — Petal count — Exhibits double flowers with approximately 45 petals under normal conditions. Petal arrangement — Cupped; tightly whorled petals. Dimensions — 3.5 cm long and 2.5 cm wide. Petal shape — Obovate. Apex — Rounded to cordate. Base — Flattened, then obtuse. Petal reflex — Outer petals reflexing to a point. Petal margin — Entire; slightly undulating. Texture — Soft. Aspect — Slightly ruffled. Petal color, upon opening — Upper surface — Near RHS 11D, with the base of petal near 2B; entire surface of inner petals are colored near RHS 2B. Lower surface — Near RHS 11D, with the base of petal near 2C; entire surface of inner petals are colored near RHS 2C. Petal color, at anthesis — Upper surface — Near RHS 11D, with the base of petal near 2B; entire surface of inner petals are colored near RHS 2B. Lower surface — Near RHS 11D, with the base of petal near 2C; entire surface of inner petals are colored near RHS 2C. Fading — Not fading.

Reproductive organs:

*Stamens*.—Quantity — Approximately 30. Anthers — Shape — Narrow ovate. Length — 0.1 cm. Color — Near RHS 21B. Pollen — Many. Pollen Color — Near RHS 3A. Filaments — Color — Near RHS 8C. Length — Approximately 0.3 cm.

*Pistils*.—Quantity — Approximately 50. Length — Approximately 1.0 cm. Stigma — Shape — Ovate. Color — Near RHS 11B. Style — Length — Approximately 0.8 cm long. Color — Near RHS 18C.

*Ovary*.—Dimensions — 0.5 cm long and 0.3 cm wide. Color — Near RHS 3D.

*Receptacle*.—Shape — Pitcher-shaped. Dimensions — 0.4 cm high and 0.5 cm wide. Color — Near RHS 143D.

Hip and seed:

*Hip*.—Shape — Rounded. Dimensions — 1.0 cm long and 1.0 cm wide. Texture — Smooth. Color — Near RHS 138C.

*Seed*.—Not present.

COMPARISONS WITH THE PARENTS

The new rose plant 'GRAyllw' may be distinguished from its seed parent, an unnamed breeding line, by the following combination of characteristics:

1. 'GRAyllw' exhibits white flowers with a yellow center, whereas the flowers of the seed parent exhibit a soft pink general tonality.
2. 'GRAyllw' exhibits flowers with strongly reflexed outer petals, whereas the outer petals of the seed parent are rounded and not strongly reflexed.
3. 'GRAyllw' exhibits an upright to semi-weeping growth habit, whereas the seed parent exhibits an upright growth habit.

The new rose plant 'GRAyllw' may be distinguished from its pollen parent, an unnamed breeding line, by the following combination of characteristics:

1. 'GRAyllw' exhibits white flowers with a yellow center, whereas the flowers of the pollen parent exhibit a white general tonality with no yellow intonations.
2. 'GRAyllw' exhibits flowers with strongly reflexed outer petals, whereas the outer petals of the pollen parent are rounded and not strongly reflexed.
3. 'GRAyllw' exhibits an upright to semi-weeping growth habit, whereas the pollen parent exhibits an upright growth habit.
4. 'GRAyllw' exhibits juvenile foliage colored near RHS 135C, whereas the pollen parent exhibits juvenile foliage colored near RHS 137C.

COMPARISONS WITH THE MOST SIMILAR VARIETY OF COMMON KNOWLEDGE

Plants of the new cultivar 'GRAyllw' may be distinguished from the commercial variety *Rosa* hybrid 'GRAppl' (U.S. Plant Pat. No. 26,364) by the following combination of characteristics:

1. 'GRAyllw' exhibits white flowers with a yellow center, whereas the flowers of 'GRAppl' exhibit a purple general tonality.
2. 'GRAyllw' exhibits a petal count of approximately 45 petals, whereas 'GRAppl' typically possesses 22 petals.
3. 'GRAyllw' exhibits average leaf dimensions of 7.0 cm long and 3.5 cm wide, whereas 'GRAppl' exhibits average leaf dimensions of 13.5 cm long and 8.5 cm wide.
4. Mature field-grown 'GRAyllw' plants exhibit an average plant height of 100 cm, whereas 'GRAppl' exhibits an average plant height of 100 cm.

That which is claimed:

1. A new and distinct variety of *Rosa* hybrid plant named 'GRAyllw', as described and illustrated herein.

* * * * *